United States Patent
Castaneda et al.

(10) Patent No.: US 9,526,543 B2
(45) Date of Patent: *Dec. 27, 2016

(54) MODULAR FRACTURE FIXATION SYSTEM

(71) Applicant: Biomet C.V., Gibraltar (GI)

(72) Inventors: Javier E. Castaneda, Miami, FL (US);
Jorge L. Orbay, Coral Gables, FL (US); Edward Mebarak, Miami, FL (US); Cesare Cavallazzi, Miramar, FL (US)

(73) Assignee: Biomet C.V., Gibraltar (GI)

( * ) Notice: Subject to any disclaimer, the term of this patent is extended or adjusted under 35 U.S.C. 154(b) by 62 days.

This patent is subject to a terminal disclaimer.

(21) Appl. No.: 14/295,808

(22) Filed: Jun. 4, 2014

(65) Prior Publication Data

US 2014/0378975 A1  Dec. 25, 2014

Related U.S. Application Data

(60) Continuation of application No. 13/596,530, filed on Aug. 28, 2012, now Pat. No. 8,747,442, which is a continuation of application No. 12/701,062, filed on Feb. 5, 2010, now Pat. No. 8,419,775, which is a division of application No. 11/536,441, filed on Sep. 28, 2006, now Pat. No. 8,394,130.

(51) Int. Cl.
*A61B 17/80* (2006.01)
*A61B 17/00* (2006.01)

(52) U.S. Cl.
CPC .......... *A61B 17/80* (2013.01); *A61B 17/8061* (2013.01); *A61B 17/8042* (2013.01); *A61B 2017/00004* (2013.01)

(58) Field of Classification Search
CPC . A61B 17/80; A61B 17/8061; A61B 17/8042; A61B 2017/00004

USPC ....... 606/279, 280, 281, 282, 286, 288, 289, 606/291, 301, 70, 71, 60; 411/393; 403/362

See application file for complete search history.

(56) References Cited

U.S. PATENT DOCUMENTS

| 1,105,105 A | 7/1914 | Sherman |
| 2,329,398 A | 9/1943 | Duffy |

(Continued)

FOREIGN PATENT DOCUMENTS

| EP | 0471419 | 6/1987 |
| EP | 0773004 | 5/1997 |

(Continued)

OTHER PUBLICATIONS

SCS™/V Distal Radius Plate: Volar; Avanta, 1998.

(Continued)

*Primary Examiner* — Pedro Philogene
*Assistant Examiner* — David C Comstock
(74) *Attorney, Agent, or Firm* — Schwegman Lundberg & Woessner, P.A.

(57) ABSTRACT

A fracture fixation plate system for use on a long bone having a metaphysis and a diaphysis, includes at least one end plate having a head portion for the metaphysis, and at least one diaphyseal plate having a first end and a second end with a plurality of screw holes therebetween. The end plate includes mating structure adapted to mate with and securely couple to at least one end of the at least one diaphyseal plate. The system preferably includes several end plates and diaphyseal plates to accommodate anatomy of various sizes. A method for coupling the plates to the bone is also provided.

21 Claims, 16 Drawing Sheets

(56) References Cited

U.S. PATENT DOCUMENTS

| | | |
|---|---|---|
| 2,406,832 A | 9/1946 | Hardinge |
| 2,486,303 A | 10/1949 | Longfellow |
| 2,526,959 A | 10/1950 | Kirebzi |
| 3,488,779 A | 1/1970 | Christensen |
| 3,561,437 A | 2/1971 | Orlich |
| 3,695,259 A | 10/1972 | Yost |
| 3,741,205 A | 6/1973 | Markolf et al. |
| 4,219,015 A | 8/1980 | Steinemann |
| 4,506,662 A | 3/1985 | Anapliotis |
| 4,565,193 A | 1/1986 | Streli |
| 4,683,878 A | 8/1987 | Carter |
| 4,776,330 A | 10/1988 | Chapman et al. |
| 4,781,183 A | 11/1988 | Casey et al. |
| 4,794,919 A | 1/1989 | Nilsson |
| 4,800,874 A | 1/1989 | David et al. |
| 4,867,144 A | 9/1989 | Karas et al. |
| 4,955,886 A | 9/1990 | Pawluk |
| 4,957,497 A | 9/1990 | Hoogland et al. |
| 4,988,351 A | 1/1991 | Paulos et al. |
| 5,002,544 A | 3/1991 | Klaue et al. |
| 5,006,120 A | 4/1991 | Carter |
| 5,015,248 A | 5/1991 | Burstein et al. |
| 5,041,114 A | 8/1991 | Chapman et al. |
| 5,053,036 A | 10/1991 | Perren et al. |
| 5,127,914 A | 7/1992 | Calderale et al. |
| 5,129,899 A | 7/1992 | Small et al. |
| 5,151,103 A | 9/1992 | Tepic et al. |
| 5,190,544 A | 3/1993 | Chapman et al. |
| 5,197,966 A | 3/1993 | Sommerkamp |
| 5,209,751 A | 5/1993 | Farris et al. |
| 5,304,180 A | 4/1994 | Slocum |
| 5,312,438 A | 5/1994 | Johnson |
| 5,324,291 A | 6/1994 | Ries et al. |
| 5,352,231 A | 10/1994 | Brumfield et al. |
| 5,364,398 A | 11/1994 | Chapman et al. |
| 5,364,399 A | 11/1994 | Lowery et al. |
| 5,462,547 A | 10/1995 | Weigum |
| 5,474,553 A | 12/1995 | Baumgart |
| 5,484,439 A | 1/1996 | Olson et al. |
| 5,527,311 A | 6/1996 | Procter et al. |
| 5,549,610 A | 8/1996 | Russell et al. |
| 5,558,674 A | 9/1996 | Heggeness et al. |
| 5,578,036 A | 11/1996 | Stone et al. |
| 5,586,985 A | 12/1996 | Putnam et al. |
| 5,601,553 A | 2/1997 | Trebing et al. |
| 5,616,142 A | 4/1997 | Yuan et al. |
| 5,616,144 A | 4/1997 | Yapp et al. |
| 5,620,445 A | 4/1997 | Brosnahan et al. |
| 5,665,088 A | 9/1997 | Gil et al. |
| 5,676,667 A | 10/1997 | Hausman |
| 5,709,682 A | 1/1998 | Medoff |
| 5,709,686 A | 1/1998 | Talos et al. |
| 5,718,705 A | 2/1998 | Sammarco |
| 5,733,287 A | 3/1998 | Tepic et al. |
| 5,741,259 A | 4/1998 | Chan |
| 5,772,662 A | 6/1998 | Chapman et al. |
| 5,827,286 A | 10/1998 | Incavo et al. |
| 5,853,413 A | 12/1998 | Carter et al. |
| 5,906,644 A | 5/1999 | Powell |
| 5,931,839 A | 8/1999 | Medoff |
| 5,938,664 A | 8/1999 | Winquist et al. |
| 5,941,878 A | 8/1999 | Medoff |
| 5,968,047 A | 10/1999 | Reed |
| 5,975,904 A | 11/1999 | Spiegel |
| 6,001,099 A | 12/1999 | Huebner |
| 6,093,201 A | 7/2000 | Cooper et al. |
| 6,096,040 A | 8/2000 | Esser |
| 6,206,881 B1 | 3/2001 | Frigg et al. |
| 6,221,073 B1 | 4/2001 | Weiss et al. |
| D443,060 S | 5/2001 | Benirschke et al. |
| 6,270,499 B1 | 8/2001 | Leu et al. |
| 6,283,969 B1 | 9/2001 | Grusin et al. |
| 6,340,362 B1 | 1/2002 | Pierer et al. |
| 6,344,042 B1 | 2/2002 | Curtis et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,379,359 B1 | 4/2002 | Dahners |
| 6,383,186 B1 | 5/2002 | Michelson |
| 6,436,100 B1 | 8/2002 | Berger |
| 6,440,135 B2 | 8/2002 | Orbay et al. |
| 6,468,278 B1 | 10/2002 | Muckter |
| 6,508,819 B1 | 1/2003 | Orbay |
| 6,527,775 B1 | 3/2003 | Warburton |
| 6,599,290 B2 | 7/2003 | Bailey et al. |
| 6,623,486 B1 | 9/2003 | Weaver et al. |
| 6,645,208 B2 | 11/2003 | Apfelbaum et al. |
| 6,669,700 B1 | 12/2003 | Farris et al. |
| 6,699,249 B2 | 3/2004 | Schlapfer et al. |
| 6,712,820 B2 | 3/2004 | Orbay |
| 6,767,351 B2 | 7/2004 | Orbay et al. |
| 6,821,278 B2 | 11/2004 | Frigg et al. |
| 6,866,665 B2 | 3/2005 | Orbay |
| 7,044,951 B2 | 5/2006 | Medoff et al. |
| 7,090,676 B2 | 8/2006 | Huebner et al. |
| 7,604,657 B2 | 10/2009 | Orbay et al. |
| 7,635,381 B2 | 12/2009 | Orbay |
| 7,867,261 B2 | 1/2011 | Sixto et al. |
| 8,062,296 B2 | 11/2011 | Orbay et al. |
| 8,128,628 B2 | 3/2012 | Freid et al. |
| 8,394,098 B2 | 3/2013 | Orbay et al. |
| 8,394,130 B2* | 3/2013 | Orbay .................... A61B 17/80 606/280 |
| 8,419,775 B2* | 4/2013 | Orbay .................... A61B 17/80 606/281 |
| 8,747,442 B2* | 6/2014 | Orbay .................... A61B 17/80 606/281 |
| 2001/0011172 A1 | 8/2001 | Orbay et al. |
| 2002/0013586 A1 | 1/2002 | Justis et al. |
| 2002/0032446 A1 | 3/2002 | Orbay |
| 2002/0156474 A1 | 10/2002 | Wack |
| 2003/0040748 A1 | 2/2003 | Aikins |
| 2003/0060828 A1 | 3/2003 | Michelson |
| 2003/0073999 A1 | 4/2003 | Putnam |
| 2003/0083661 A1 | 5/2003 | Orbay et al. |
| 2003/0105461 A1 | 6/2003 | Putnam |
| 2003/0153918 A1 | 8/2003 | Putnam |
| 2004/0030339 A1 | 2/2004 | Wack et al. |
| 2004/0059334 A1 | 3/2004 | Weaver et al. |
| 2004/0059335 A1 | 3/2004 | Weaver et al. |
| 2004/0087953 A1 | 5/2004 | Singhatat et al. |
| 2004/0097937 A1 | 5/2004 | Pike et al. |
| 2004/0102778 A1 | 5/2004 | Huebner et al. |
| 2004/0167521 A1 | 8/2004 | De Windt |
| 2004/0167522 A1 | 8/2004 | Niederberger et al. |
| 2004/0193155 A1 | 9/2004 | Castaneda |
| 2004/0210221 A1 | 10/2004 | Kozak et al. |
| 2004/0230196 A1 | 11/2004 | Martello |
| 2004/0260291 A1 | 12/2004 | Jensen |
| 2005/0010226 A1 | 1/2005 | Grady et al. |
| 2005/0049593 A1 | 3/2005 | Duong et al. |
| 2005/0049594 A1 | 3/2005 | Wack et al. |
| 2005/0085818 A1 | 4/2005 | Huebner |
| 2005/0154392 A1 | 7/2005 | Medoff et al. |
| 2005/0182405 A1 | 8/2005 | Orbay et al. |
| 2005/0187551 A1 | 8/2005 | Orbay et al. |
| 2005/0240187 A1 | 10/2005 | Huebner et al. |
| 2006/0100625 A1 | 5/2006 | Ralph et al. |
| 2006/0189987 A1 | 8/2006 | Orbay et al. |
| 2006/0229619 A1 | 10/2006 | Orbay et al. |
| 2006/0235404 A1 | 10/2006 | Orbay et al. |
| 2007/0260244 A1 | 11/2007 | Wolter |

FOREIGN PATENT DOCUMENTS

| | | |
|---|---|---|
| EP | 0955013 | 11/1999 |
| EP | 1464295 | 10/2004 |
| FR | 2367479 | 5/1978 |
| GB | 2072514 | 10/1981 |
| JP | 11299804 | 2/1999 |
| JP | 11128245 | 5/1999 |
| JP | 11-290359 | 10/1999 |
| JP | 2003052709 | 2/2003 |

(56) References Cited

FOREIGN PATENT DOCUMENTS

| WO | WO99/44529 | 9/1999 |
|----|------------|--------|
| WO | WO02096309 | 12/2002 |
| WO | WO2004045389 | 6/2004 |
| WO | WO/2006/102081 | 9/2006 |
| WO | WO-2006102081 A1 | 9/2006 |

OTHER PUBLICATIONS

The Distal Radius Plate Instrument and Implant Set; Technical Guide, SYNTHES®, Paoli, PA 1995.
Advances in distal Radius Fracture Management(D); transcript of American Academy of Orthopaedic Surgeons 2001; Conference pp. 134-151, Feb. 28, 2001, including article by Matthew D. Putnam, MD, entitled "Repair and Rehabilitation of Distal Radius Fractures: The Role of Subchondral Fixation" at pp. 144-147.
Summary of Safety and Effectiveness Information for Synthes Condylar Buttress Plates; Synthes USA.
Biomechanics in Uniaxial Compression of Three Distal Radius Volar Plates; D. Osada; S. Fujita, K. Tamai, A. Iwamoto, K. Tomizawa, K. Saotome; The Journal of Hand Surgery, 2004.
Surgical Innovations; Advances in Distal Radius Fixation; J. Orbay, MD; Mar./Apr. 2003.
"The Titanium Distal Radius Plate", Technique Guide, SYNTHES RTM, Paoli, PA, 1995.
SCS/D Distal Radius Plate System; Avanta; 1997.
3.5 MM LCP Proximal Tibia Plates, Technique Guide, SYNTHES, 2004.
Distal Femoral Locked Plating System, POLYAX™ Wide Angle Freedom, 2005 DePuy Orthopaedics, Inc., 5M0606, 0612-54-501 (Rev.1).
Proximal Tibia Plate Instrument and Implant Set, SYNTHES Sep. 2000.
SYNTHES 2002 Catalog, pp. 2b-35, 2b-59.
U.S. Appl. No. 11/536,441, 312 Amendment filed Jan. 23, 2013, 3 pgs.
U.S. Appl. No. 11/536,441, Final Office Action mailed Jun. 25, 2009, 8 pgs.
U.S. Appl. No. 11/536,441, Non Final Office Action mailed Mar. 24, 2008, 6 pgs.
U.S. Appl. No. 11/536,441, Notice of Allowance mailed Mar. 1, 2012, 8 pgs.
U.S. Appl. No. 11/536,441, Notice of Allowance mailed Sep. 4, 2009, 6 pgs.
U.S. Appl. No. 11/536,441, Notice of Allowance mailed Oct. 31, 2012, 5 pgs.
U.S. Appl. No. 11/536,441, Preliminary Amendment filed Nov. 21, 2007, 9 pg.
U.S. Appl. No. 11/536,441, PTO Response to Rule 312 Communication mailed Feb. 11, 2013, 2 pgs.
U.S. Appl. No. 11/536,441, Response filed Feb. 18, 2009 to Restriction Requirement mailed Feb. 5, 2009, 10 pgs.
U.S. Appl. No. 11/536,441, Response filed Jun. 17, 2008 to Non Final Office Action mailed Mar. 24, 2008, 13 pgs.
U.S. Appl. No. 11/536,441, Response filed Jul. 31, 2009 to Final Office Action mailed Jun. 25, 2009, 12 pgs.
U.S. Appl. No. 11/536,441, Response filed Nov. 11, 2008 to Restriction Requirement mailed Oct. 17, 2008, 10 pgs.
U.S. Appl. No. 11/536,441, Restriction Requirement mailed Feb. 5, 2009, 7 pgs.
U.S. Appl. No. 11/536,441, Restriction Requirement mailed Oct. 17, 2008, 5 pgs.
U.S. Appl. No. 11/557,429, Non Final Office Action mailed Apr. 28, 2010, 7 pgs.
U.S. Appl. No. 11/557,429, Notice of Allowance mailed Sep. 10, 2010, 4 pgs.
U.S. Appl. No. 11/557,429, Preliminary Amendment filed Nov. 27, 2007, 3 pgs.
U.S. Appl. No. 11/557,429, Response filed Jun. 24, 2010 to Non Final Office Action mailed Apr. 28, 2010, 9 pgs.
U.S. Appl. No. 12/701,062, 312 Amendment filed Nov. 29, 2012, 9 pgs.
U.S. Appl. No. 12/701,062, Final Office Action mailed Jun. 15, 2012, 6 pgs.
U.S. Appl. No. 12/701,062, Non Final Office Action mailed Mar. 5, 2012, 5 pgs.
U.S. Appl. No. 12/701,062, Notice of Allowance mailed Jan. 3, 2013, 5 pgs.
U.S. Appl. No. 12/701,062, Notice of Allowance mailed Aug. 31, 2012, 5 pgs.
U.S. Appl. No. 12/701,062, Preliminary Amendment filed Feb. 5, 2010, 7 pgs.
U.S. Appl. No. 12/701,062, Response filed May 17, 2012 to Non Final Office Action mailed Mar. 5, 2012, 19 pgs.
U.S. Appl. No. 12/701,062, Response filed Aug. 8, 2012 to Final Office Action mailed Jun. 15, 2012, 6 pgs.
U.S. Appl. No. 13/596,530, 312 Amendment filed Mar. 17, 2014, 3 pgs.
U.S. Appl. No. 13/596,530, Non Final Office Action mailed May 23, 2013, 4 pgs.
U.S. Appl. No. 13/596,530, Notice of Allowance mailed Jan. 14, 2014, 5 pgs.
U.S. Appl. No. 13/596,530, PTO Response to Rule 312 Communication mailed May 7, 2014, 2 pgs.
U.S. Appl. No. 13/596,530, Response filed Sep. 10, 2013 to Non Final Office Action mailed May 23, 2013, 6 pgs.
U.S. Appl. No. PCT/US2007/078967, International Preliminary Report on Patentability mailed Oct. 8, 2008, 3 pgs.
International Application Serial No. PCT/US2007/078967, International Search Report mailed Apr. 15, 2008, 1 pg.
International Application U.S. Appl. No. PCT/US2007/078967, Written Opinion mailed Apr. 15, 2008, 4 pgs.

* cited by examiner

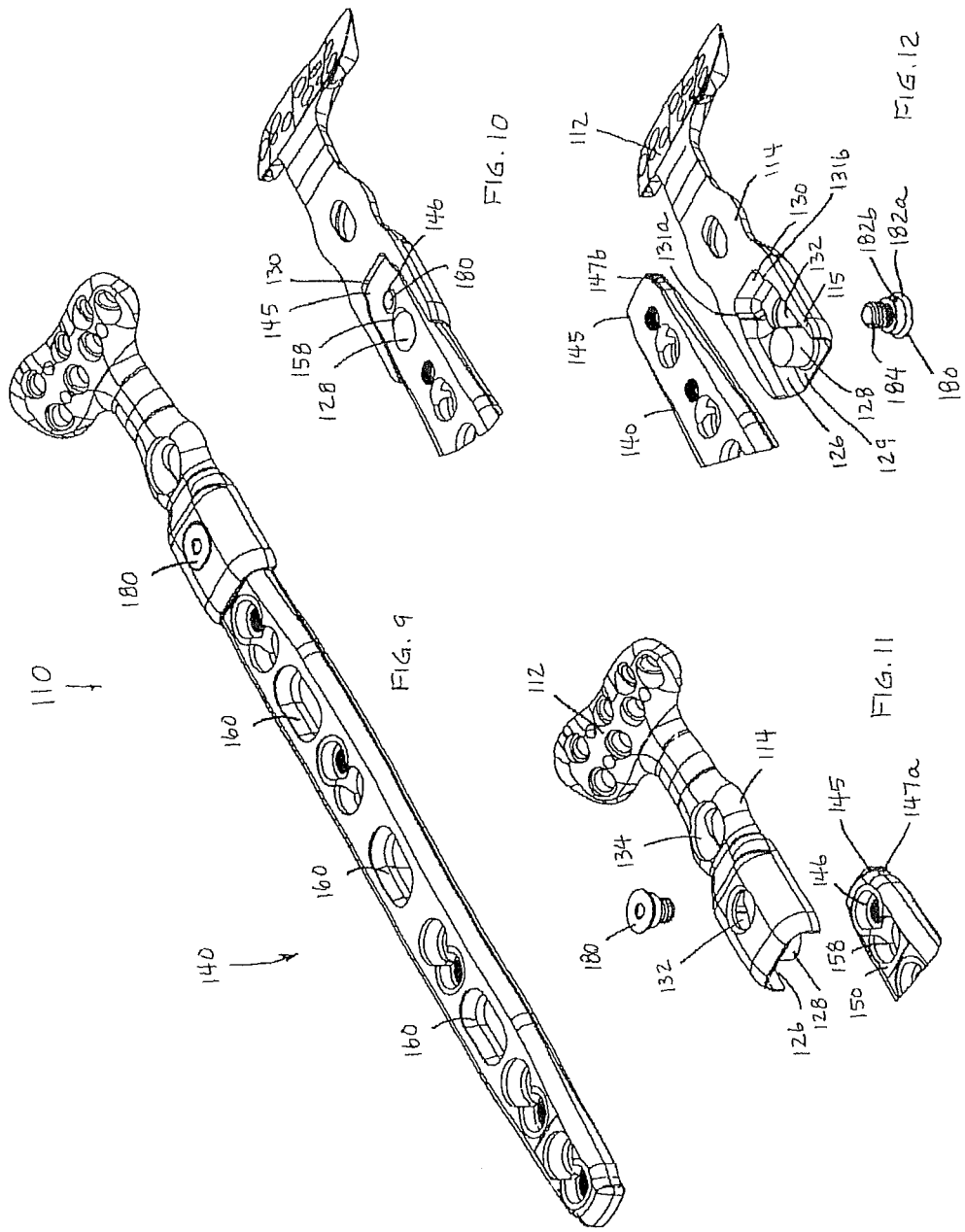

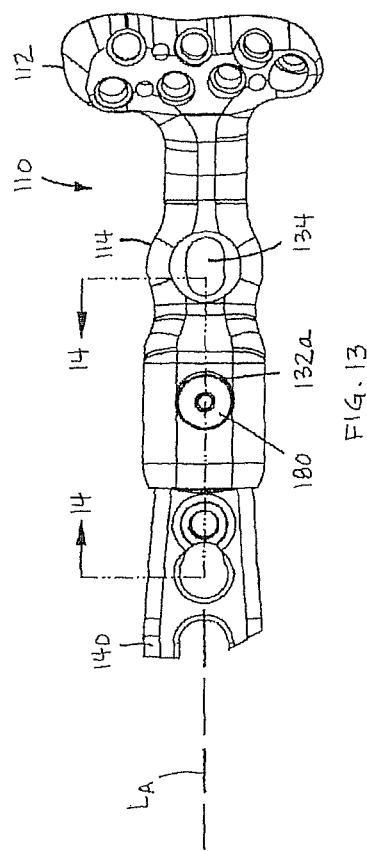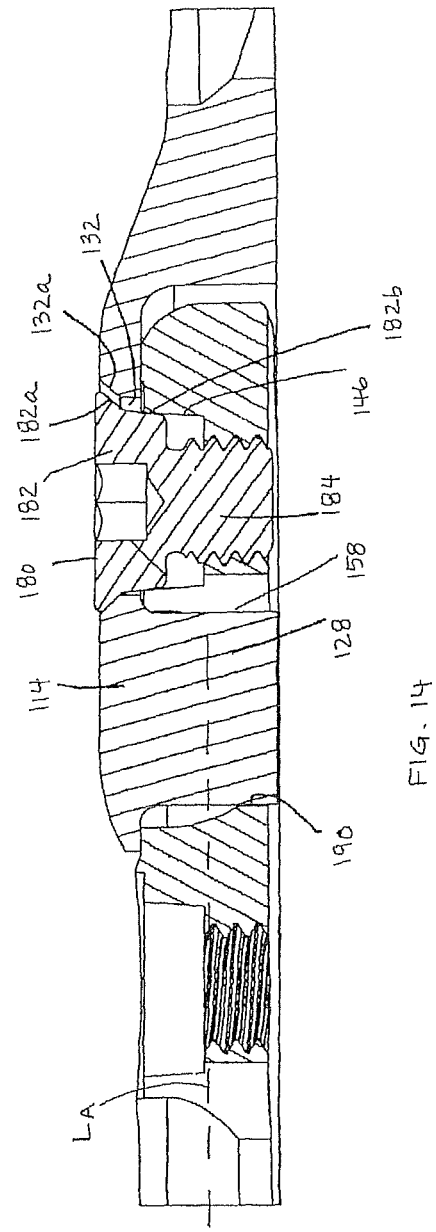

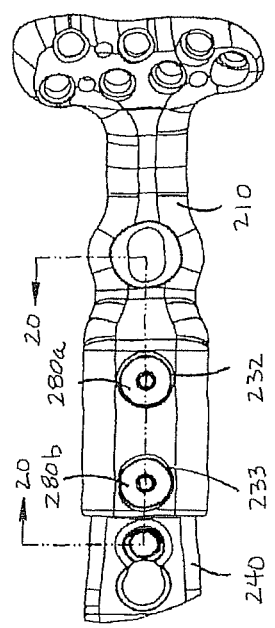
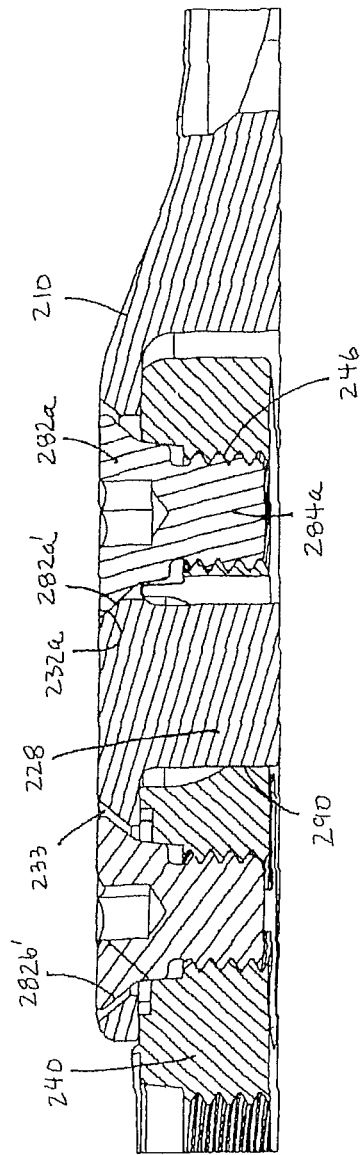
FIG. 19
FIG. 20

MODULAR FRACTURE FIXATION SYSTEM

CROSS-REFERENCE TO RELATED APPLICATIONS

This application is a continuation of U.S. Ser. No. 13/596,530, filed Aug. 28, 2012, which is a continuation of U.S. Ser. No. 12/701,062, filed Feb. 5, 2010, now issued as U.S. Pat. No. 8,419,775, which is a divisional of U.S. Ser. No. 11/536,441, filed Sep. 28, 2006, now issued as U.S. Pat. No. 8,394,130, all of which are hereby incorporated by reference herein in their entireties.

This application is related to U.S. Ser. No. 11/378,703, filed Mar. 17, 2006, now issued as U.S. Pat. No. 8,394,098, and U.S. Ser. No. 11/082,401, filed Mar. 17, 2005, now issued as U.S. Pat. No. 8,062,296, both of which are hereby incorporated by reference herein in their entireties. This application is also related to U.S. Ser. No. 10/985,598, filed Nov. 10, 2004, now issued as U.S. Pat. No. 7,635,381, U.S. Ser. No. 11/040,779, filed Jan. 21, 2005, now abandoned, and U.S. Ser. No. 11/466,905, filed Aug. 24, 2006, now issued as U.S. Pat. No. 7,604,657, which are also hereby incorporated by reference herein in their entireties.

BACKGROUND OF THE INVENTION

1. Field of the Invention

This invention relates broadly to surgical implants. More particularly, this invention relates to a bone fracture fixation system.

2. State of the Art

Fracture to the metaphyseal portion of a long bone can be difficult to treat. Improper treatment can result in deformity and long-term discomfort.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate placed against the bone, and screws extending from the plate into holes drilled in the bone fragments to provide stabilized fixation of the fragments.

In some cases, a relatively proximal diaphyseal portion as well as the distal metaphyseal portion of the radius may be fractured. Similarly, a relatively distal diaphyseal portion as well as the proximal portion of the humerus may be fractured. In these cases, diaphyseal plates are often used in conjunction with an appropriate metaphyseal plate. There is a disadvantage, however, in using two separate plates rather than one. It results in unsupported bone between the two plates. The resultant load is supported by the bone between the plates in a concentrated manner. Thus, it would be desirable to provide an integrated plate that shares the load across the entire implant for both metaphyseal and diaphyseal fractures.

U.S. Pat. No. 5,190,544 to Chapman et al. describes a modular plating system including a metaphyseal plate and a diaphyseal plate that are interconnected via a dovetail slot and then secured to the bone with cortical bone screws to lock the plates together. The integrity of such a system is subject to loosening in the event the bone screws loosen their engagement with the bone, e.g., through micromotion. Furthermore, if the bone is of poor quality, e.g., as a result of multiple fractures along the bone portion underlying the components, integrity between the components may never be accomplished. In addition, the metaphyseal component which receives an end of the diaphyseal plate is significantly thicker (approximately 75% percent thicker) and wider (approximately 35% wider) than the diaphyseal plate, providing an undesirably thick metaphyseal plate and creating a potentially irritating transition in two dimensions from the metaphyseal plate to the diaphyseal plate where the metaphyseal plate ends.

SUMMARY OF THE INVENTION

It is therefore an object of the invention to provide a modular fixation system.

It is another object of the invention to provide a modular fixation system that desirably aligns and stabilizes multiple bone fragments in a fracture to permit proper healing.

It is also an object of the invention to provide a modular fixation system that does not rely on the bone for locking the modular components together.

It is a further object of the invention to provide a modular fixation system in which the components are coupled together in a very stable manner to effect a rigid assembly.

It is yet another object of the invention to provide a modular fixation system that, in view of manufacturing variations, will eliminate play between coupled components to increase the load transfer between the coupled components.

It is a yet a further object of the invention to provide a modular fixation system that will not irritate the tissue.

It is an additional object of the invention to provide improved fixation systems that accommodate the anatomical structure of the metaphysis and diaphysis of the radius and humerus.

In accord with these and other objects, which will be discussed in detail below, various embodiments of a modular fracture fixation system are provided. The modular system of the invention is described with respect to exemplar embodiments specifically adapted for the radius and humerus bones.

In exemplar embodiments for the radius bones, the modular fracture fixation system includes a plurality of different sized distal radius plates (e.g., volar plates or dorsal plates) and a plurality of different sized diaphyseal plates. The distal radius plates are generally T-shaped having a head and a stem substantially transverse thereto. The end of the stem is provided with a mating structure whereby an end of a diaphyseal plate can be coupled to the distal radius plate. The surgeon can select an appropriate size distal radius plate and an appropriate size diaphyseal plate and secure them together prior to implantation on the bone to form a unified distal radius and diaphyseal plate customized for the patient. This overcomes the disadvantage of using separate distal radius and diaphyseal plates and allows for a wide variety of different sizes while using the minimum number of components. It is an important aspect of the invention that the distal radius plate and diaphyseal plate be joined without reliance on the bone to join them. Otherwise, the tight interface and coupling between the plates could be compromised based on the quality of the bone, which may be fractured beneath the location of the coupling or which may be osteoporotic. In order to secure the distal radius plate and diaphyseal plate together independent of the bone, set screw holes are provided at both ends of the diaphyseal plates. In addition, suitable mating structure is provided at the end of the radius plate stem including a non-threaded set screw hole and an intersecting socket. The two plates are mated by inserting one end of the diaphyseal plate into the socket of the distal radius plate stem, then inserting one or more connection set screws through the non-threaded screw hole(s) in the stem to engage the threaded set screw hole in the end of the diaphyseal plate. In certain embodiments, means are provided to eliminate any play between the plates, including posts, flats, and non-circular holes, and multiple set screw holes and connection set screws may be provided.

In exemplar embodiments for the humerus bones, the modular fracture fixation system includes a plurality of different sized proximal humerus plates and a plurality of different sized humeral diaphyseal plates. The humeral plates have a head portion, preferably provided with a plurality of threaded holes and suture holes, and a stem portion provided with longitudinally displaced screw holes. The end of the stem is provided with a mating structure whereby an end of a diaphyseal plate can be coupled to the humeral plate. The surgeon can select an appropriate size humeral plate and an appropriate size diaphyseal plate and secure them together prior to implantation on the bone to form a unified humeral plate customized for the patient. This overcomes the disadvantage of using separate plates for the metaphyseal and diaphyseal portions of the humerus and allows for a wide variety of different sizes while using the minimum number of components. For reasons advanced above, it is an important aspect of the invention that the proximal humerus plate and diaphyseal plate be joined without reliance on the bone to join them. In a coupling system similar to the radius system, mating structure is provided at the end of the humerus plate stem including a non-threaded screw hole and an intersecting socket. The two plates are mated by inserting one end of the diaphyseal plate into the socket of the plate stem, then inserting one or more connection set screws through the non-threaded screw holes in the stem to engage the threaded set screw hole in the end of the diaphyseal plate. Preferably, means are provided to eliminate any play between the plates, and multiple connection screw holes and connection screws may be provided.

Additional objects and advantages of the invention will become apparent to those skilled in the art upon reference to the detailed description taken in conjunction with the provided figures.

BRIEF DESCRIPTION OF THE DRAWINGS

FIG. 9 is a perspective view of a second embodiment of a modular plate system according to the invention;

FIG. 10 is a broken bottom perspective view of the embodiment of FIG. 9;

FIG. 11 is a broken top perspective exploded view of the embodiment of FIG. 9;

FIG. 12 is a broken bottom perspective exploded view of the embodiment of FIG. 9;

FIG. 13 is a broken top view of the embodiment of FIG. 9;

FIG. 14 is a section view across line 14-14 in FIG. 13;

FIG. 19 is a broken top view of the embodiment of FIG. 15;

FIG. 20 is a section view across line 20-20 in FIG. 19;

DETAILED DESCRIPTION OF THE PREFERRED EMBODIMENTS

Figure 1:
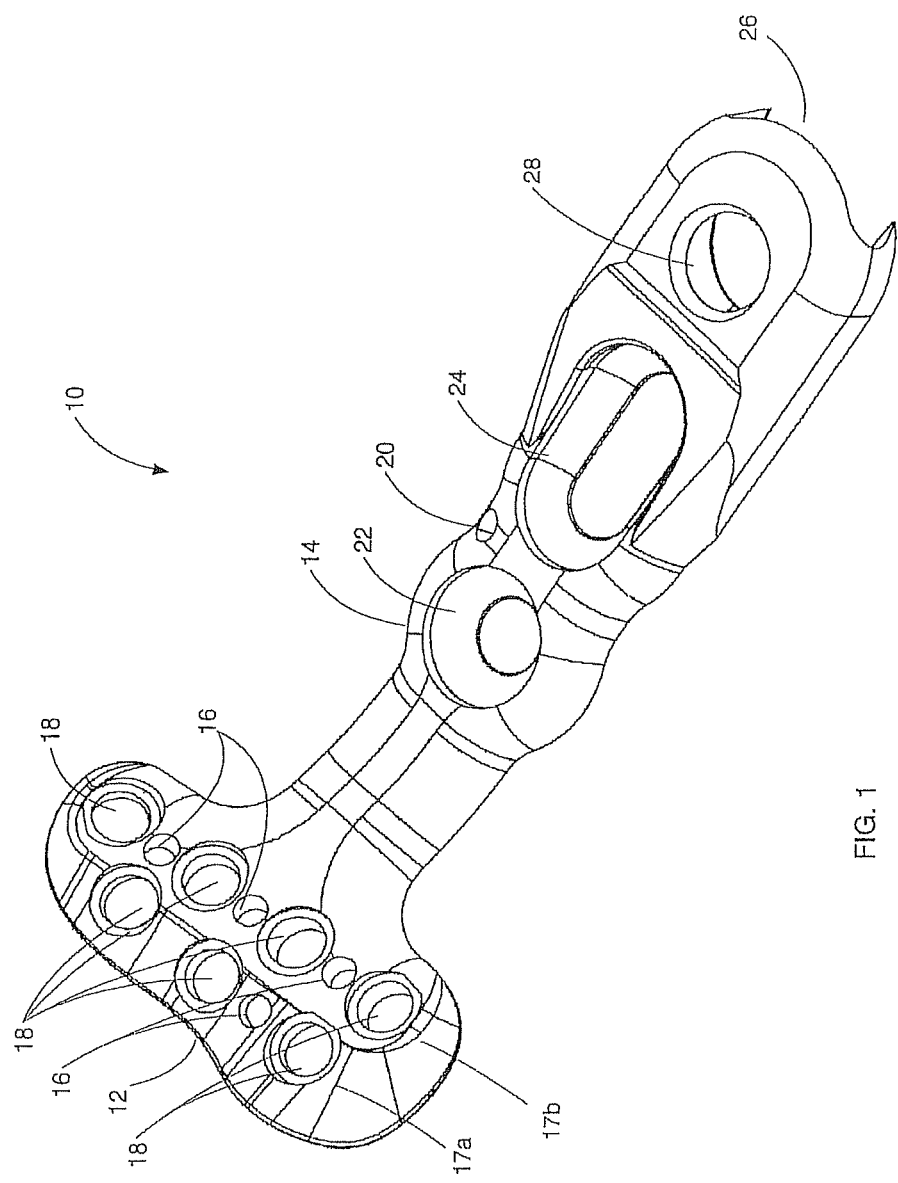
FIG. 1 is a top perspective view of a distal radius volar plate according to the invention.
Figure 2:
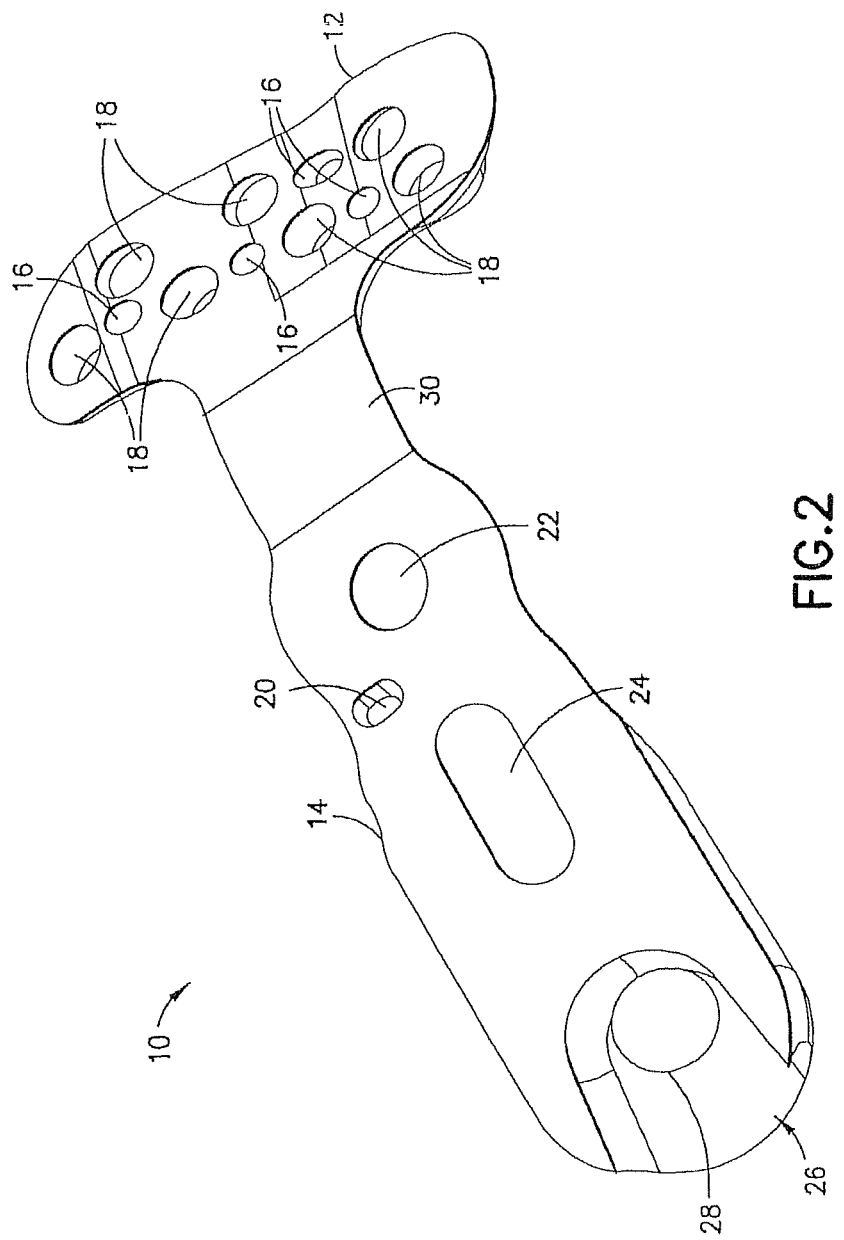
FIG. 2 is a bottom perspective view of the volar plate.

Turning now to FIGS. 1 and 2, a distal radius volar fixation plate (or generally any 'end' plate or metaphyseal plate) 10 includes a distal head portion 12 and a proximal stem portion 14. In a preferred embodiment, the plate 10 corresponds to the plate described in previously incorporated U.S. Ser. No. 10/985,598. However, other metaphyseal plates for different locations on the radius bone or even for placement on different bones can be used.

The head portion 12 of the volar fixation plate 10 shown has a plurality of alignment holes 16 which are dimensioned to closely accept K-wires in a fixed angle relationship and two longitudinally offset rows 17a, 17b of screw holes 18 for receiving fixation elements therethrough. In a preferred embodiment, the screw holes 18 are threaded, and as such are specifically adapted to receive locking screws and/or pegs that lock in axial alignment relative to the plate.

The stem portion 14 has at least one alignment hole 20 dimensioned to closely accept a K-wire and may optionally include one or more (two as illustrated) bone screw holes 22, 24. That is, the stem may be substantially shorter than shown and does not need to include a bone screw hole. The free end of the stem portion 14 includes a socket in the form of a slot 26 (for receiving an end of the diaphyseal plate 40, described below) and an orthogonal set screw hole 28 intersecting the slot. As shown in FIGS. 1-8, the slot 26 is open to the proximal end of the stem portion, and preferably is also open on the bottom side of the stem portion as well.

From FIGS. 1-8, it will be appreciated that the top side (FIG. 1) of the volar plate 10 has a topography of curved surfaces and recesses surrounding some of the holes to provide a low profile when seated on the anatomical bone surface. The bottom side (FIG. 2) of the head portion 12 is likewise constructed to conform to the anatomy, while the stem portion 14, however presents a smooth surface. The bottom of the head portion 12 lies in a first plane and the stem portion 14 lies in a second plane. A neck 30 transitions between the two planes. The angle between the two planes is preferably approximately 25 degrees.

The alignment holes and the bone screw holes are used as described in previously incorporated U.S. Ser. No. 10/985, 598. The slot 26 and the set screw hole 28 are used in conjunction with a diaphyseal plate and a set screw as described in more detail below.

Figure 3:
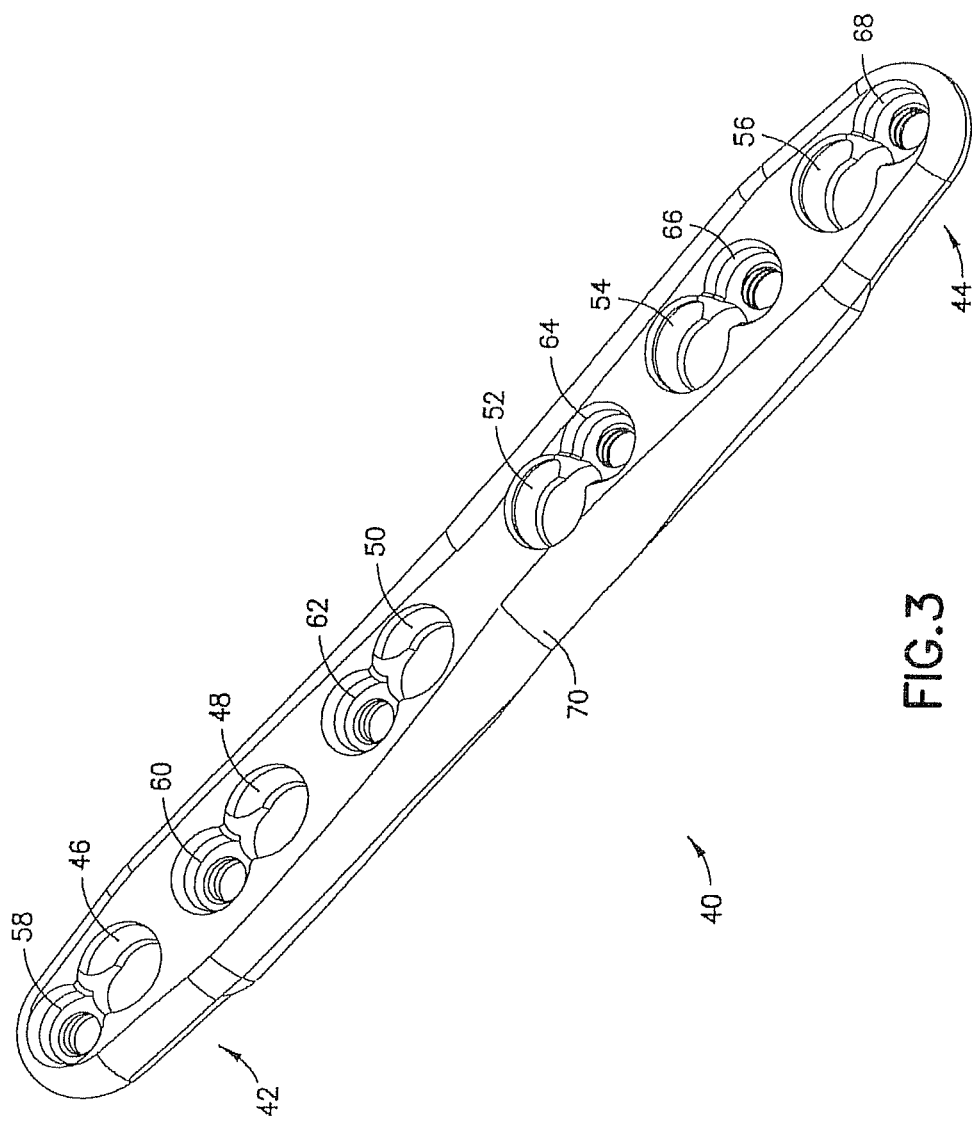
FIG. 3 is top perspective view of a diaphyseal plate according to the invention.
Figure 4:
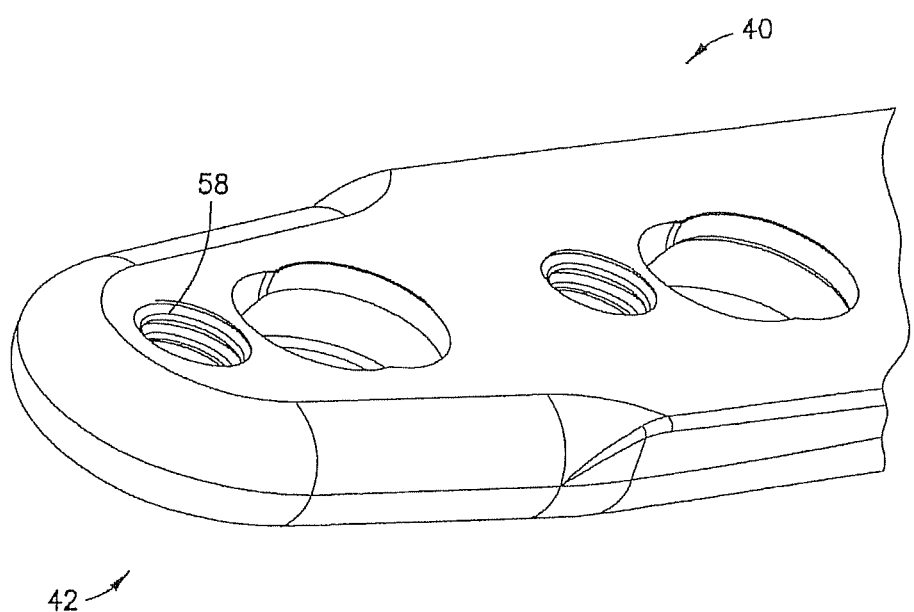
FIG. 4 is an enlarged broken bottom perspective view of an end of the diaphyseal plate.
Figure 5:
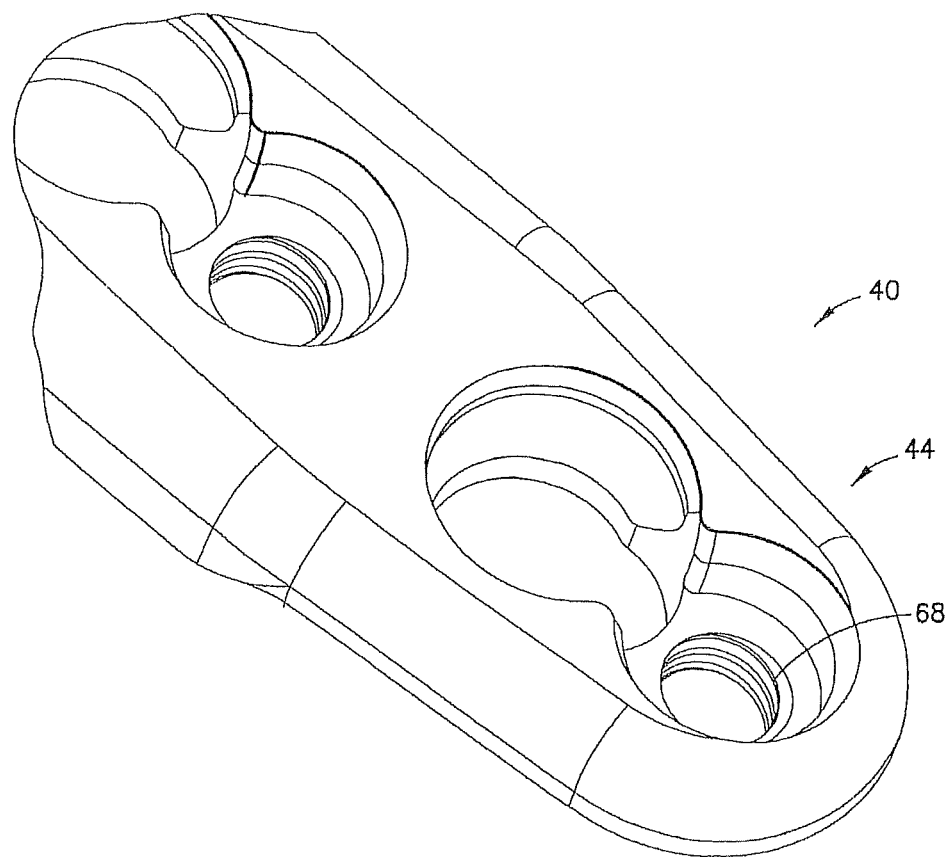
FIG. 5 is an enlarged broken top perspective view of an end of the diaphyseal plate.

Turning now to FIGS. 3-5, an exemplary diaphyseal plate (or fragment plate) 40 according to the invention is illustrated. The diaphyseal plate 40 is an elongate plate having a first end 42 and a second end 44. A plurality of bone screw holes 46, 48, 50, 52, 54, 56 are spaced along the length of the plate for receiving bone screws, and a threaded set screw hole 58, 60, 62, 64, 66, 68 is arranged adjacent each bone screw hole. More particularly, such screw holes are preferably any of the screw holes and associated locking systems described in U.S. Pub. No. 20050187551 A1, incorporated by reference herein, for the reasons and advantages provided therein, although any suitable bone screw hole may be used.

As illustrated, the shape of the diaphyseal plate 40 and the arrangement of holes are preferably longitudinally symmetrical about a mid point 70. Each set screw hole is provided on a side of a bone screw hole closer to an end of the diaphyseal plate than the midpoint of the plate, with a set screw hole 58, 68 specifically being located at each end of the plate. As seen best in FIGS. 4 and 5, the ends 42, 44 of the plate are tapered as well as rounded. The taper occurs over a significant length which permits both a bone screw hole 46, 56 and a set screw hole 58, 68 to be located in the tapered ends 42, 44 of each plate. Comparing FIGS. 4 and 5 with FIGS. 1 and 2, it will be appreciated that the ends 42, 44 of the plate 40 are shaped and dimensioned to fit neatly into the slot 26 of the volar plate 10 with the set screw hole 58, 68 of the plate 40 aligning with the set screw hole 28 of the plate 10. This is illustrated more clearly in FIG. 6. The taper at the end of the diaphyseal plate 40 permits the remainder of the diaphyseal plate and the stem 14 of the end plate 10 to have substantially the same width, e.g., approximately 0.43" for a distal radius fixation system. It is noted that both ends 42, 44 of the diaphyseal plate preferably have the same shape and features. Thus either end 42, 44 may be inserted into the slot 26 of the plate.

Figure 6:
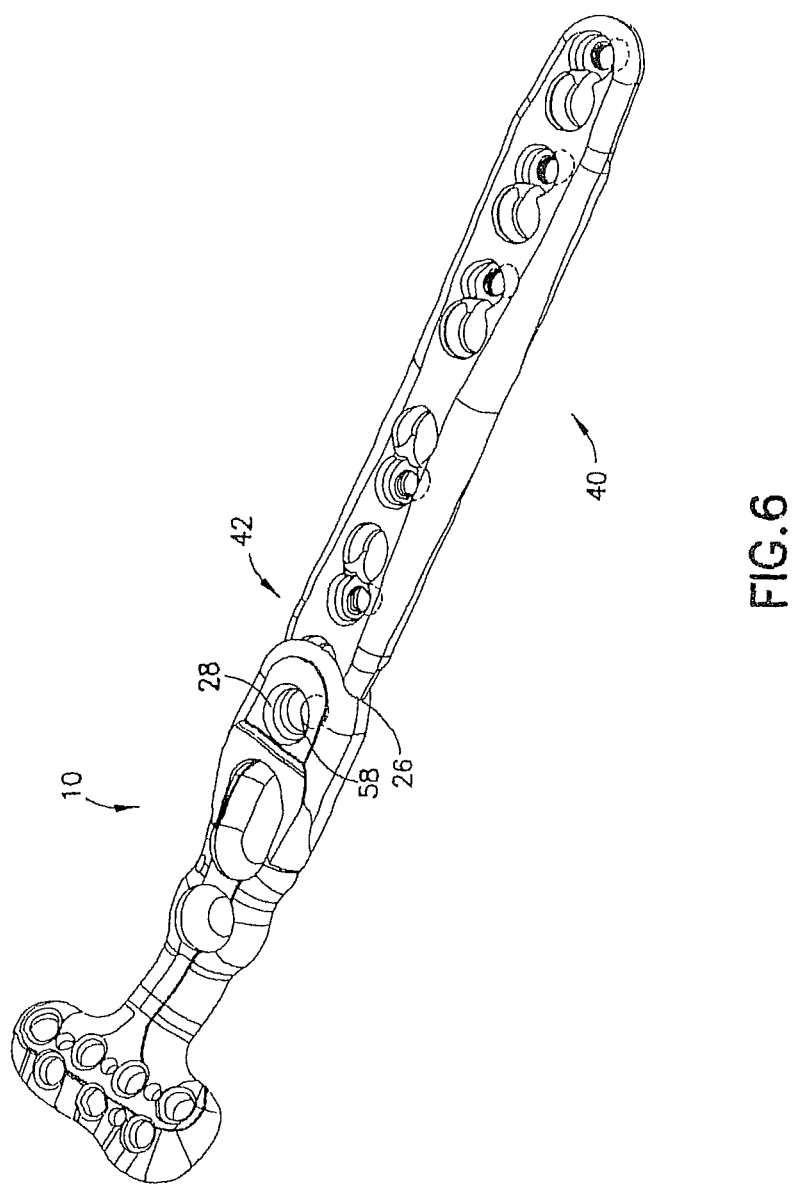
FIG. 6 is a top perspective view of the volar plate with the diaphyseal plate inserted into the slot at the end of the volar plate stem.
Figure 7:
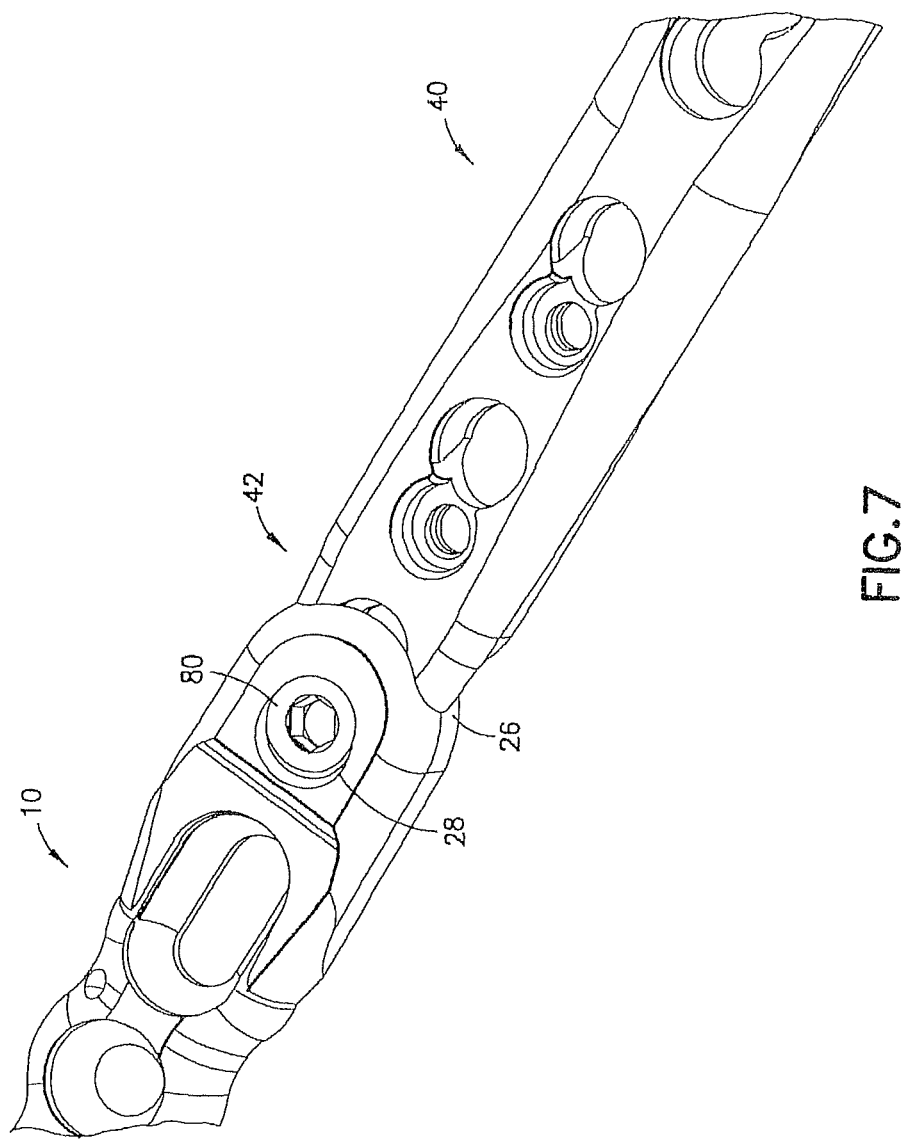
FIG. 7 is an enlarged broken top perspective view showing the mating of the volar plate and the diaphyseal plate with a set screw.
Figure 8:
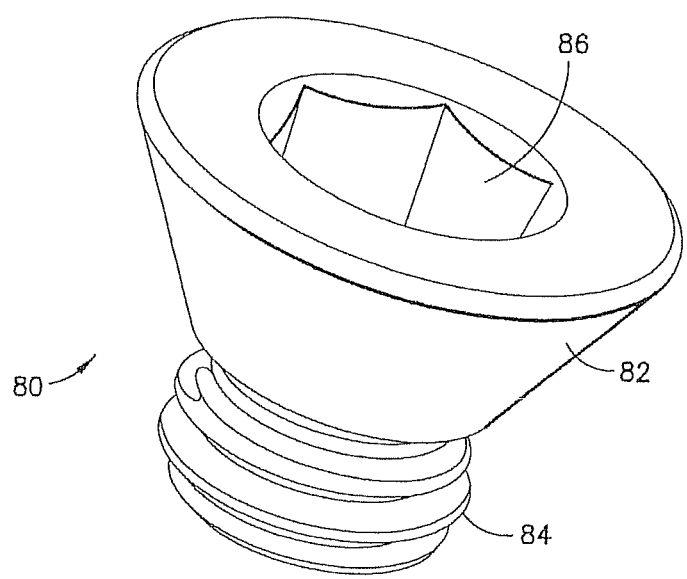
FIG. 8 is an enlarged perspective view of the set screw.

FIG. 6 shows the end 42 of the plate 40 inserted into the slot 26 of the plate 10. The tapered and rounded end 42 of the plate 40 is shaped and dimensioned to fit neatly into the slot 26 through the bottom of the volar plate 10 with the threaded set screw hole 58 of the plate 40 aligning with the unthreaded set screw hole 28 of the plate 10. When the two plates are arranged as shown in FIG. 6, a set screw 80 is inserted into the hole 28 as shown in FIG. 7. When so inserted, the set screw 80 is threaded into the threaded set screw hole 58 in the plate 40. This secures the two plates together so that they function as a single piece. It is an important aspect of the invention that the distal radius plate and diaphyseal plate be joined without reliance on the bone to join them. Otherwise, the tight interface and coupling between the plates could be compromised based on the quality of the bone, e.g., where such bone is fractured beneath the location of the coupling or where the bone is osteoporotic.

The set screw 80 has a frustoconical head 82 from which depends a threaded stem 84. The head 82 has a hex socket 86 adapted to receive a driver (not shown). The set screw provides a secure lock between the two plates independent of the bone.

By having a threaded set screw hole 58, 68 located near each end of the diaphyseal plate, each such hole can be used to lock the diaphyseal plate to the volar plate, or may alternatively be used to lock an adjacent bone screw in a bone screw hole 46, 56 in place.

In accord with the invention, the end plate 10 at the slot 26 and the diaphyseal plate 40 are substantially similar in thickness, preferably within approximately 30% of each other, and more preferably approximately 26% (end plate=0.145" and diaphyseal plate=0.115"). The relatively close thicknesses are possible, for one reason, in that the end plate does not need to support the compressive forces of bone screws at that location. Rather, as discussed above, the set screws used exert a substantially smaller force on the upper thinner portion of the end plate than would a cortical screw under compressive load.

It is appreciated that the end plate and diaphyseal plate components, separately machined or otherwise formed from each other, will invariably differ, within tolerances, from their specified designs. Such variations from predefined dimensions may cause the components when assembled to have some 'play'. Any play between the components reduces the ability of the assembly to transfer load from one component to the other. Play also results in micromovement of the components that may hamper the healing process. In view of the above, the second and third embodiments are provided.

Turning now to FIGS. 9 through 14, the second embodiment of a modular plate system, including an end plate 110 and a diaphyseal plate 140, is shown. The end plate 110 includes stem portion 114 that is larger in width and thickness at a free end opposite the head portion 112. The underside of the free end 115 is open defining a socket in the form of a cavity 126 into which a post 128 descends. The surface 129 from which the post descends is flat. The cavity 126 tapers in width and defines at an end a portion 130 stepped down in width. The end portion defines opposing flat parallel wall portions 131a, 131b. The stem portion 114 includes a slightly oval set screw hole 132 into the cavity, located between the post 128 and the stepped down portion 130 of the cavity. The centers of the post 128 and set screw hole 132 are intended to be offset by a first distance within a defined tolerance. An oval cortical bone screw hole 134 is also provided in the thinner portion of the stem.

The diaphyseal plate 140 is similar to plate 40, but includes ends 145 stepped down in width and sized to fit within the stepped down portion 130 of the cavity 126. Such ends 145 include short opposing parallel flat sides 147a, 147b. In addition, the upper surface 150 of the diaphyseal plate over the last threaded set screw hole 146 and bone screw hole 158 (i.e., that portion that will be received within the cavity, as described below) is flat to seat stably against flat surface 129 in the cavity. The last set screw hole 146 and bone screw hole 158 are offset from each other by a second distance within a defined tolerance. The second distance is slightly larger than the first defined distance. Also, as an option, several of the screw holes, e.g., 160 (FIG. 9), along the diaphyseal plate are non-locking oblong cortical screw holes.

The set screw 180 includes a head 182 and a shank 184. Head 182 defined by two frustoconical sections: the upper frustoconical section 182a is angled to seat against the rim 132a of the set screw hole 132, whereas the lower frustoconical section 182b is angled to seat within the upper portion 146a of the set screw hole 146 at the end of the diaphyseal plate.

Referring to FIGS. 13 and 14, in assembly, an end 145 of the diaphyseal plate is positioned with the cavity 126 of the end plate 110 and the post 128 is inserted into bone screw hole 158 such that it extends transverse to the longitudinal axis $L_A$. Given the differences between the first and second defined offset distances, the threads of set screw hole 146 do not perfectly align with the center of non-threaded set screw hole 132. However, the shank 184 of the set screw 180 is easily maneuvered through set screw hole 132 and into engagement within the threads of the screw hole 146. As the upper section 182a of the head 182 contacts the rim 132a of screw hole 132, the set screw 180 provides a force to push the post 128 of the end plate 110 against the diaphyseal plate (at 190) causing significant interference so as to remove any play. As a result, in axial load, all force is transferred from the end plate to the diaphyseal plate. In addition, when the end plate is subject to torsional force, the flat sides 147a, 147b of the diaphyseal plate being in close contact with flat walls 131a, 131b limits rotation of the components relative to each other. The walls 131a, 131b are of sufficient length to accommodate the range of tolerances to which the components may be manufactured; i.e., so that flat sides 147a, 147b are always adjacent some portion of the flat walls 131a, 131b.

Turning now to FIGS. 15 through 20, the third embodiment of a modular plate system, including an end plate 210 and a diaphyseal plate 240, is shown. The end plate 210 is substantially similar to end plate 110, with the following differences. The enlarged free end includes a widthwise tapered cavity 226 provided with a post 228, and two slightly oblong non-threaded set screw holes 232, 233 entering the cavity 226 one on either side of the post 228. Post 228 and screw hole 232 are offset by a first distance within a defined tolerance. The thinner portion of the end plate includes a preferably oblong non-threaded bone screw hole 234.

The diaphyseal plate 240 is similar to plate 140 with the following differences. The ends 245 are tapered and rounded and do not include the stepped end. The last set screw hole 246 and bone screw hole 258 are offset from each other by a second distance within a defined tolerance. Another machine threaded screw hole 260 is provided independent of a cooperative non-threaded bone screw hole. The screw hole 260 is preferably defined by two spaced apart cantilevers 262, 264 set off from the interior of the plate by slots 266, 268 extending generally parallel to the longitudinal axis of the plate. In addition, a recess 270 is provided at the upper portion of the screw hole 260.

Referring to FIGS. 19 and 20, in assembly, an end 245 of the diaphyseal plate is positioned with the cavity 226 of the end plate 210 through the bottom of the end plate and the post 228 is inserted into bone screw hole 258. Given the differences between the first and second defined offset distances, the threads of set screw hole 246 do not perfectly align with the center of non-threaded set screw hole 232. However, the shank 284a of the set screw 280a is easily maneuvered through set screw hole 232 and into engagement within the threads of the screw hole 246. As the upper section 282a' of the head 282a contacts the rim 232a of screw hole 232, the set screw 280a provides a force to push the post 228 of the end plate 210 against the diaphyseal plate (at 290) causing significant interference so as to remove any play. As a result, in axial load, all force is transferred from the end plate 210 to the diaphyseal plate 240. The second set screw 280b is inserted into screw hole 233. When set screw 280b is fully seated, the chamfer at the lower side of head portion 282b' contacts the chamfer about screw hole 233 regardless of the position of the end plate 210 relative to the diaphyseal plate 240. Thus, when the end plate 240 is subject to torsional force, screw 280b limits rotation of the components relative to each other.

In one exemplar embodiment, the end plate 210 at the socket 226 has a thickness of approximately 0.17" and the diaphyseal plate 240 has a thickness of 0.135" at the portion positioned within the socket. As such, in accord with the first embodiment, the thickness of the coupling is less than approximately 30 percent and approximately 26 percent. The second embodiment can be constructed with similar relative dimensions.

Figure 15:
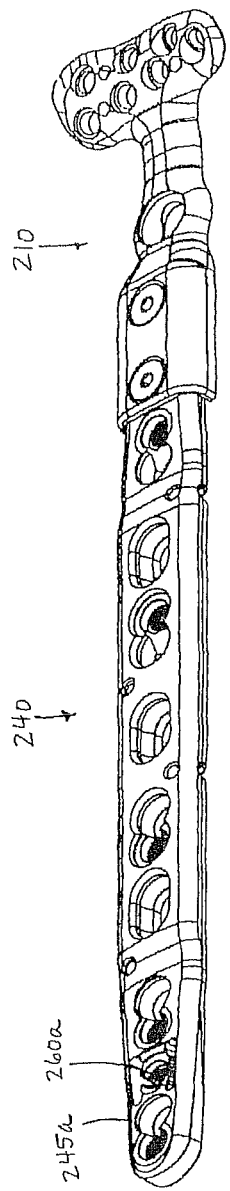
FIG. 15 is a perspective view of a third embodiment of a modular plate system according to the invention.
Figure 16:
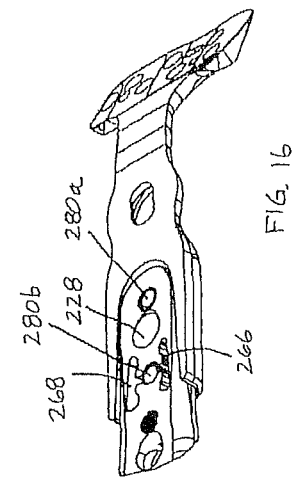
FIG. 16 is a broken bottom perspective view of the embodiment of FIG. 15.
Figure 18:
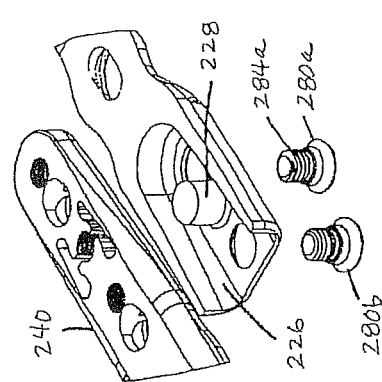
FIG. 18 is a broken bottom perspective exploded view of the embodiment of FIG. 15.
Figure 17:
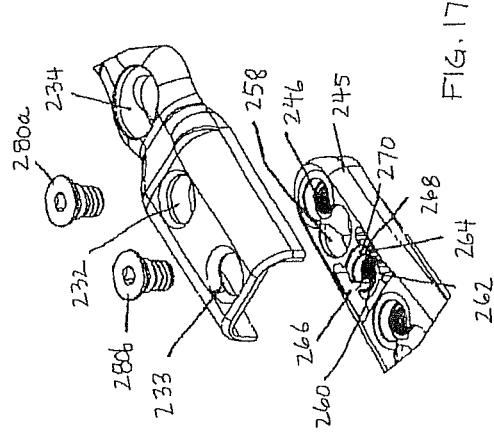
FIG. 17 is a broken top perspective exploded view of the embodiment of FIG. 15.

In addition, referring to FIG. 15, the end 245a of the diaphyseal plate 240 which is not coupled to the end plate 210 also includes a machine threaded screw 260a, as described above with respect to 260. Such screw hole 260a and the associated framelike structure of the plate thereabout decreases the rigidity of the plate at that location. As such, any cortical screw implanted into bone at the end 245a, and the bone thereabout, will be subject to reduced maximum stress. In addition, the end 245a of the plate can be adjusted in rigidity. By inserting a set screw or other insert into screw hole 260a the diaphyseal plate is made more rigid. Recess 270 allows countersinking of the head of such set screw. For example, without the set screw the plate may have a flexibility of 0.003 inch, whereas with the set screw inserted, the flexibility is reduced to 0.001 inch. It is appreciated that in some circumstances it is desirable to have a diaphyseal plate that is flexible at its ends, while in other instances, e.g., when the fracture is more comminuted, it is advantageous to have a plate that is less flexible during the healing process. In addition, assuming that a comminuted bone fracture completely heals after a period of time, it may be advantageous to have a plate that after healing allows the bone to function under normal conditions and does not produce high stress concentrations at the cortical screw-bone interface. As such, the set screw or insert can be bio-absorbable, maintaining needed fixation during the healing process, followed by absorption such that the plate has higher stiffness during healing and is more flexible thereafter. The resultant plate system would be less likely to result in refracture due to the weakening attributed with drilling holes in the bone and then point loading at those holes. Diaphyseal plates with such cantilevered set screw holes can be used with or without a modular end plate to achieve the benefits described above.

Figure 21:
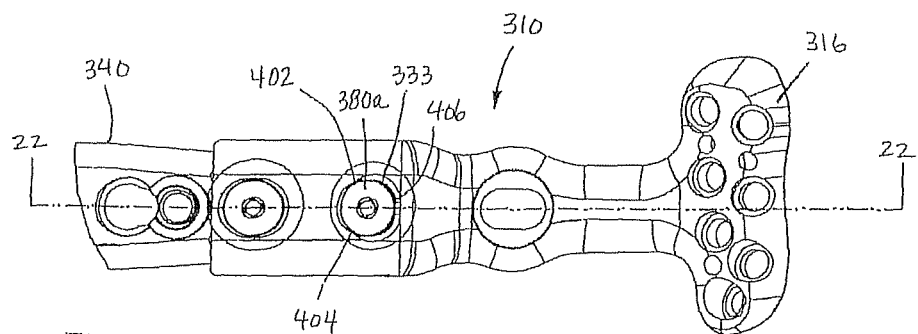
FIG. 21 is a broken top view of a fourth embodiment of a modular plate system according to the invention.
Figure 22:
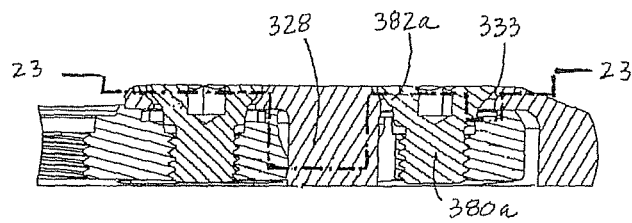
FIG. 22 is a broken section view along line 22-22 in FIG. 21.
Figure 23:
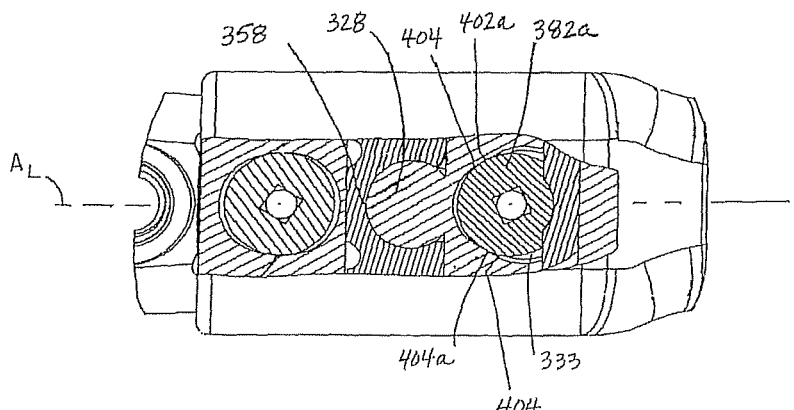
FIG. 23 is a top view of the modular connection of the fourth embodiment, illustrated by the removal of material along line 23-23 in FIG. 22.

Referring now to FIGS. 21 through 23, a fourth embodiment of a distal radius modular fixation system, substantially similar to the third embodiment, is shown. The system includes a modular metaphyseal end plate 310 and a diaphyseal plate 340. The end plate 310 is preferably the same as end plate 210 with the following difference. Screw hole 333, instead of being oblong (as is hole 233), is a countersunk chevron (or rounded triangular) shape. In a preferred embodiment, chevron hole 333 includes three faces 402, 404, 406 defined by a generally 60° triangle. The faces 402, 404 are directed away from the head portion 316 of the end plate and provide two lateral points of contact 402a, 404a between the conical flat head 382a of the distal modular set screw 380a and the end plate 310. During coupling of the end and diaphyseal plates 310, 340, in addition to downward compression, the head 382a of the distal set screw 380a imparts laterally opposing force at contact points 402a, 404a about the longitudinal symmetry plane $A_L$ (FIG. 23). In addition, because of the angular orientation of the contact faces 402, 404, the head 382a of the distal set screw also imparts a longitudinal force along the symmetry plate $A_L$. Alternately, the chevron hole 333 could be reversed in direction such that contact surfaces 402, 404 are directed toward the head portion 316 of the end plate.

Turning now to FIGS. 24 through 29, an embodiment of a proximal humeral modular fixation system is shown. The system includes a proximal humeral metaphyseal modular end plate 510 and a diaphyseal plate 540.

Figure 24:
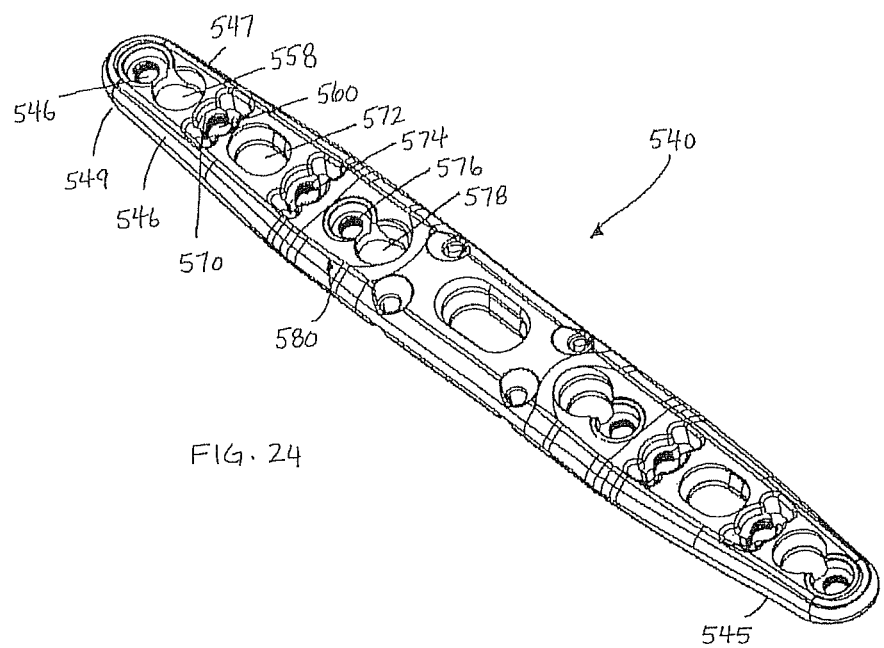
FIG. 24 is a top perspective view of a diaphyseal plate for a fifth embodiment of the invention.

Referring to FIG. 24, the diaphyseal plate 540 includes features similar to plate 240. Plate 540 includes two end portions 545 each with sides 547, 549 tapering at preferably approximately 6°. Each end portion 545 preferably includes in the following order from its end: (i) a combination of a set screw hole 546 and bone screw hole 558, (ii) a first cantilevered screw hole 560 (similar to hole 260) provided with an upper countersink recess 570, (iii) an oblong screw hole 572, (iv) a second cantilevered screw hole 574, and (v) a second combination of a set screw hole 576 and a bone screw hole 578. Bone screw holes 558, 578 are preferably non-threaded and also structured to receive cortical screws in a fixed angle orientation substantially perpendicular to the bone contacting surface 580 of the plate. Other screw holes and K-wire and suture holes are also preferably provided along the length of the diaphyseal plate.

Figure 25:
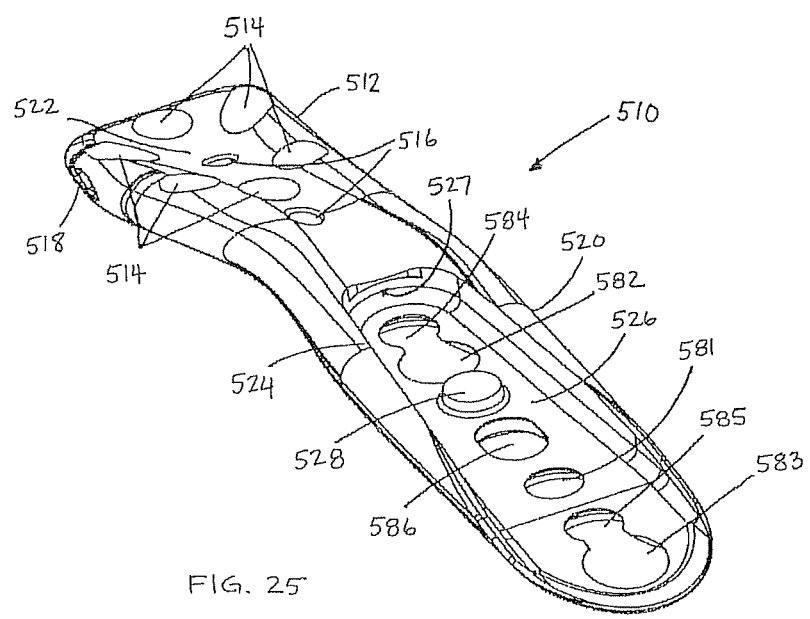
FIG. 25 is a bottom perspective view of a metaphyseal proximal humeral end plate for modular assembly with the diaphyseal plate of FIG. 24.

Referring to FIG. 25, the humeral end plate 510 includes a head portion 512 preferably provided with threaded holes 514, fixed angle K-wire holes 516, and suture holes 518, as described in previously incorporated U.S. Ser. No. 11/466, 905. The end plate also includes a stem portion 520. The head portion 512 is angled relative to the stem portion 520 such that the bone contacting surface 522 of the head portion is angled upward at approximately 10°-18°, and most preferably approximately 15°, relative to the bone contacting surface 524 or long axis of the stem portion providing the head portion and stem portion each in substantially parallel alignment relative to the underlying anatomy when properly positioned at the proximal humerus. The stem portion 520 includes a lower socket (or recess) 526 for receiving the end portion 545 of the diaphyseal plate 540. The socket 526 tapers in width at approximately 6° to correspond to the tapered sides at the end portion 545. The socket 526 defines a proximal undercut 527 to receive the end of the diaphyseal plate. An integrated post 528 extends downward from the top of the plate into the socket 526 for alignment within the countersink recess 570 of the first cantilevered screw hole 560 of the diaphyseal plate, as described in more detail below. A first (middle) slightly eccentric tapered set screw hole 581 is provided for alignment over the second cantilevered screw hole 574. Passing holes 582, 583 sized to permit passage of a cortical screw completely therethrough and into the bone screw holes 558, 578 in the diaphyseal plate 540 are provided in alignment therefor, and second and third tapered holes 584, 585 are provided adjacent the passing holes and in alignment with set screw holes 546, 576. An oblong screw hole 586 is provided for alignment over oblong screw hole 572 in the diaphyseal plate.

Figure 26:
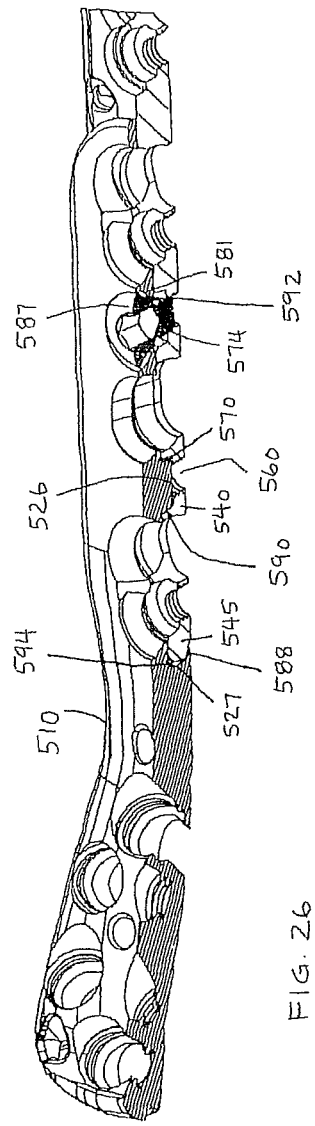
FIG. 26 is a perspective longitudinal section view of the preliminary modular assembly of the plates shown in FIGS. 24 and 25.
Figure 29:
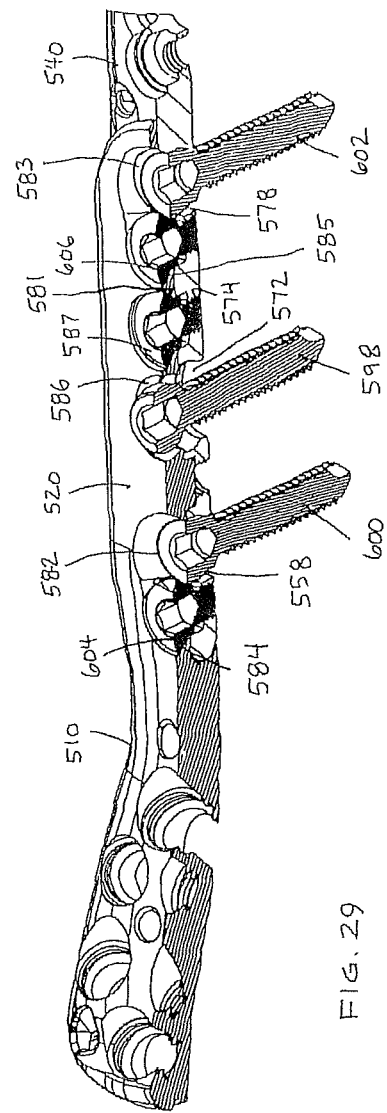
FIG. 29 is a perspective longitudinal section view of the modular assembly of the plates shown in FIGS. 24 and 25 with additional fasteners.
Figure 27:
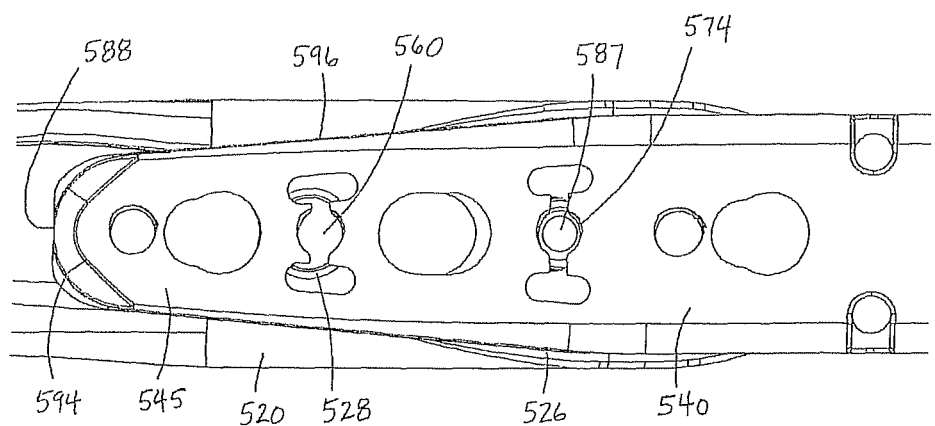
FIG. 27 is a broken bottom view of the preliminary modular assembly of FIG. 26.
Figure 28:
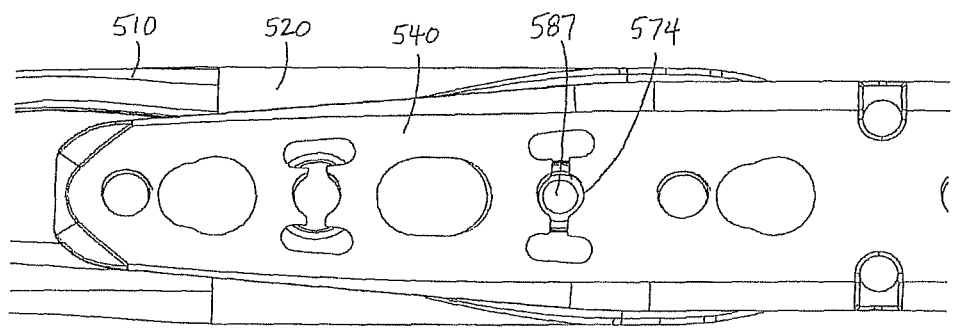
FIG. 28 is a broken bottom view of the modular assembly of the plates shown in FIGS. 24 and 25.

Referring to FIGS. 25 through 27, in assembly, an end 545 of the diaphyseal plate 540 is positioned into the socket 526 through the bottom of the end plate 510 with the post 528 inserted into the recess 570 at the top of the first cantilevered screw hole 560. The end of the diaphyseal plate 540 seats within the undercut 527 defined at the proximal end of the socket 526. A set screw 587 is then inserted into the first tapered set screw hole 581 and preliminarily engaged within the second cantilevered threaded screw hole 574 thereabeneath thus defining three points of contact to stabilize the assembly, as follows. A first point of contact 588 is defined between the end of the diaphyseal plate 540 and its contact with the socket 526 adjacent the undercut 527. A second point of contact 590 is defined between the post 528 and the proximal side of recess 570. A third point of contact 592 is defined between the head of set screw 587 and the distal side of tapered eccentric screw hole 581. Referring to FIG. 26, while these three points stabilize the assembly, it is appreciated that initially there may be gaps between the tip of the diaphyseal plate and the undercut (at 594) and between the tapered sides of the diaphyseal plate and the tapered recess (at 596). However, as shown in FIGS. 28 and 29, as the set screw 587 is driven into the second cantilevered hole 574, the force of the tapered head of the set screw against the tapered surface of the screw hole 581 drives the two plates 510, 540 relative to each other to eliminate the gaps 594, 596 shown in FIGS. 26 and 27. The result is a very rigid assembly which transfers force from the end plate to the diaphyseal plate. Thus, with a single set screw the two plates are held together such that the modular plate assembly can be positioned on the bone prior to the introduction of any cortical screws.

Referring to FIG. 29, after positioning the modular assembly on the bone, a hole is drilled for a multidirectional cortical screw 598 to be inserted through vertically offset oblong screw holes 572, 586. Hole 586 is sized to capture the head of screw 598 such that the screw head is held within hole 586 on the stem 520 of the humeral end plate 510. The oblong shape of the hole 586 allows the modular assembly to be shifted longitudinally under the head of the screw 598 until the screw is tightened to fix the location of the assembly on the bone. Screw holes are then drilled through passing holes 582, 583 and aligned with screw holes 558, 578, and fixed angle cortical screws 600, 602 are inserted through the screw holes into the bone. The heads of the cortical screws 600, 602 pass through passing holes 582, 583 and are captured by the screw holes 558, 578, providing further compression of the diaphyseal portion of the modular assembly against the diaphysis of the bone. Set screws 604, 606 are finally inserted into holes 546, 576 and underlying set screw holes 584, 585 (but preferably do not interfere or extend into the underlying bone), further coupling the end and diaphyseal plates together in a manner which is independent of the bone and also preventing potential backout of the cortical screws 600, 602.

According to an important aspect of the invention, the plates 10 (110, 210, 310, 510) and 40 (140, 240, 340, 540) are arranged in a kit containing several different size plates 10 and several different size diaphyseal plates 40. According to the presently preferred embodiment, three different size volar plates are provided: standard, wide, and narrow. The volar plate and humeral plates are also provided in left and right versions. A plurality of different length diaphyseal plates are also provided. The diaphyseal plates may be straight or curved. For example, the plate may be curved in the plane of the plate to match the radius of curvature of the volar side of the radius bone, e.g., r=23 inches over approximately eighty percent of the length of the plate. The diaphyseal plates can be used alone or in combination with the metaphyseal end plates. When used together, distal and mid-shaft fractures can be covered with one integrated plate (e.g., the two plates coupled to each other as shown in FIG. 7 or 25). Thus, the loads are shared by the combined plate rather than the bone between two plates. The load is thereby spread out rather than concentrated on the bone between two plates. The modularity of the different size plates allows for the assembly of a wide variety of combinations using only a few different sizes. By way of example, and not by limitation, three different width volar plates packed together with five different length diaphyseal plates can be used to construct fifteen different size combination plates using only eight different size pieces. Similar advantage can be provided in a humeral or other bone system.

According to an alternate embodiment of the invention, the metaphyseal end plate is not required to include a socket in the form of a slot or cavity for receiving an end portion of the diaphyseal plate. Rather, a discrete coupler with sockets at two of its sides can be provided between the end and diaphyseal plates. The coupler operates to "splice" together the metaphyseal end plate and the diaphyseal plate. The advantage is that the metaphyseal end plate for use in the system can be a standard component without modification, and can therefore be used alone without the diaphyseal plate. Thus, the surgical tray will need fewer of the more expensive volar plates. In addition, the coupler allows "splicing" of multiple diaphyseal plates together to make one extra long plate.

There have been described and illustrated herein embodiments of a fixation plate, and particularly plates for fixation of distal radius and proximal humerus fractures. While particular embodiments of the invention have been described, it is not intended that the invention be limited thereto, as it is intended that the invention be as broad in scope as the art will allow and that the specification be read likewise. Thus, while particular preferred materials, dimensions, and relative angles for particular elements of the system have been disclosed, it will be appreciated that other materials, dimensions, and relative angles may be used as well. Further, while the invention has been described with respect to distal volar radius and proximal humerus plates, the invention may include other 'end' plates suitable in size and shape for placement at other metaphyseal locations, e.g., the dorsal side of the distal radius, the femur and the tibia. In addition, end plates of shapes other than described may also be used, such as lateral and medial columns (generally 'L'-shaped), and plates having a flared or forked head, provided such end plates are dimensioned and configured for placement at the metaphysis. In addition, while a particular number of screw holes in the end plate and diaphyseal plate have been described, it will be understood a different numbers of screw holes may be used. Also, fewer or more threaded holes (for pegs or locking screws) may be used. In addition, while particular preferred angles between the head and stem or shaft of the end plates have been disclosed, other angles can also be used. Further, while various connection structures between the end plate and diaphyseal plate have been disclosed, it is appreciated other connection structures can be used as well. That is, provided that a rigid assembly can be maintained, for example, with three points of contact, the post can be eliminated, and the various screw holes can be re-arranged, reconfigured, or altered in number. Also, while the term diaphyseal plate has been used for plates structured and intended for placement on the diaphysis of a long bone, the term is also intended to encompass any fragment plate structured for placement on a long bone and intended for coupling with a metaphyseal end plate in a manner claimed. It will therefore be appreciated by those skilled in the art that yet other modifications could be made to the provided invention without deviating from its scope.

What is claimed is:

1. A fracture fixation plate system for use on a long bone, the long bone having a surface, the system comprising:
   a) a first plate including a bone contacting first surface and an opposite second surface, a first end portion and a second end portion, a plurality of screw holes extending between the first and second surfaces, the first surface configured for seating superficially over the surface of the long bone, the first end portion defining a cavity that extends under the second surface and which includes a first coupling hole provided through the second surface and into the cavity;
   b) a second plate including a bone contacting first surface and an opposite second surface, a first end portion and a second end portion, a plurality of screw holes extending between the first and second surfaces, the first surface configured for seating superficially over the surface of the long bone, the second end portion defining a rounded end that is rounded in a direction transverse to a longitudinal axis of the second end portion, the second end portion further including a threaded second coupling hole,
   wherein when the rounded end of the second end portion is fully inserted into the cavity, the first coupling hole and second coupling hole are arranged in alignment; and
   c) a set screw inserted within the first coupling hole and in threaded engagement with the second coupling hole, the set screw sized in length to retain the first and second plates assembled together separate from the long bone.

2. A system according to claim 1, wherein:
one of the first plate and the second plate is a metaphyseal plate, and the other of the first plate and the second plate is a diaphyseal plate.

3. A system according to claim 2, wherein:
the metaphyseal plate is configured for placement on the metaphysis of the volar side of the distal radius.

4. A system according to claim 2, wherein:
the metaphyseal plate includes a head portion and a shaft portion, Wherein the head portion is angled relative to the shaft portion.

5. A system according to claim 1, wherein:
the first and second plate when retained assembled together extend along a common longitudinal axis.

6. A system according to claim 1, wherein:
the rounded end of the second end portion is rounded in a plane extending between the first and second surfaces.

7. A system according to claim 1, wherein:
the rounded end of the second end portion is shaped and dimensioned to fit neatly into the cavity.

8. A system according to claim 1, wherein:
the cavity is a socket.

9. A system according to claim 1, wherein:
the cavity tapers in width.

10. A fracture fixation plate system for use on a long bone having a metaphysis and a diaphysis, the long bone having a surface, the system comprising:
   a) a metaphyseal first plate including a bone contacting first surface and an opposite second surface, a plurality of holes extending between the first and second surfaces for receiving fixation elements that extend into the metaphysis of the long bone, the first surface of the metaphyseal first plate configured for conform for seating over the surface of the metaphysis of the long bone;
   b) a diaphyseal second plate including a bone contacting first surface and an opposite second surface, a first end portion and a second end portion, a plurality of screw holes longitudinally displaced between the first an second ends and extending between the first and second surfaces, the first surface of the diaphyseal second plate configured for seating superficially over the surface of the diaphysis of the long bone, wherein
   one of the second end portion of the first plate and the first end portion of the second plate defines a socket that extends under the second surface of the respective plate and includes a first coupling hole provided through its second surface and into the socket, and
   the other of the first plate and second plate defines a threaded second coupling hole and a rounded end rounded in a direction transverse to the longitudinal axis, and
   wherein when the rounded end is fully inserted into the socket, the first coupling hole and second coupling hole are arranged in alignment; and
   c) a set screw inserted within the first coupling hole and in threaded engagement with the second coupling hole, the set screw sized in length to retain the metaphyseal plate and diaphyseal plate assembled together separately from the long bone.

11. A system according to claim 10, wherein:
the metaphyseal plate is configured for placement on the metaphysis of the volar side of the distal radius.

12. A system according to claim 10, wherein:
the metaphyseal plate and diaphyseal plate when retained assembled together extend along a common longitudinal axis.

13. A system according to claim 10, wherein:
the rounded end is rounded in a plane extending between the first and second surfaces.

14. A system according to claim 10, wherein:
the rounded end is shaped and dimensioned to fit neatly into the cavity.

15. A system according to claim 10, wherein:
the cavity is a socket.

16. A system according to claim 10, wherein:
the cavity tapers in width.

17. A method of coupling an assembly of bone plates to a bone having a surface, comprising:
   a) providing first and second plates, the first plate having a first and second ends, the second end defining a cavity, and the second plate having first and second ends, the first end of the second plate receivable within the cavity;
   b) inserting the first end of the plate into the cavity at the second end of the first plate;
   c) first coupling the first and second plates together separately from the bone so that they are retained relative to each other in an assembly when subject to tension;
   d) attaching the coupled first and second plates to the surface of the bone with a first cortical screw, the first cortical screw having a head that seats on the first plate above the surface of the bone; and then
   e) further securing the coupled plates to the bone with a second cortical screw, the second cortical screw having a head that seats on the second plate above the surface of the bone.

18. A method according to claim 17, wherein:
one of the first and second plates is a distal radius metaphyseal plate, and the other of the first and second plates is a radial diaphyseal plate.

19. A method according to claim 17, wherein:
one of the first and second plates is a proximal metaphyseal humeral plate, and the other of the first and second plates is a humeral diaphyseal plate.

20. A method according to claim 17, wherein.
the second end of the first plate includes a first coupling hole, the first end of the second plate includes a threaded second coupling hole, and the first coupling includes inserting a set screw within the first coupling hole in the second end of the first plate and into threaded engagement with the second coupling hole in the first end of the second plate.

21. A method according to claim 20, wherein:
axial advancement of the set screw into the second coupling hole in a first direction causes movement of the first and second plates relative to each other.

* * * * *

UNITED STATES PATENT AND TRADEMARK OFFICE
CERTIFICATE OF CORRECTION

PATENT NO. : 9,526,543 B2  Page 1 of 1
APPLICATION NO. : 14/295808
DATED : December 27, 2016
INVENTOR(S) : Castaneda et al.

It is certified that error appears in the above-identified patent and that said Letters Patent is hereby corrected as shown below:

In the Claims

In Column 12, Line 56, in Claim 4, delete "Wherein" and insert --wherein--, therefor In Column 13, Line 19, in Claim 10, delete "an" and insert --and--, therefor In Column 14, Line 37, in Claim 20, delete "wherein." and insert --wherein:--, therefor Signed and Sealed this
Ninth Day of January, 2018

Joseph Matal
*Performing the Functions and Duties of the*
*Under Secretary of Commerce for Intellectual Property and*
*Director of the United States Patent and Trademark Office*